(12) United States Patent
Renaud et al.

(10) Patent No.: US 8,507,668 B2
(45) Date of Patent: Aug. 13, 2013

(54) PROCESS FOR THE SYNTHESIS OF IVABRADINE AND ADDITION SALTS THEREOF WITH A PHARMACEUTICALLY ACCEPTABLE ACID

(71) Applicant: Les Laboratoires Servier, Suresnes Cedex (FR)

(72) Inventors: Jean-Luc Renaud, Bieville-Beuville (FR); Nicolas Pannetier, Caen (FR); Sylvain Gaillard, Caen (FR); Jean-Pierre Lecouve, Le Havre (FR); Lucile Vaysse-Ludot, St-Wandrille-Rancon (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/714,950

(22) Filed: Dec. 14, 2012

(65) Prior Publication Data
US 2013/0158257 A1 Jun. 20, 2013

(30) Foreign Application Priority Data

Dec. 20, 2011 (FR) ..................... 11 03934

(51) Int. Cl.
*C07D 223/16* (2006.01)

(52) U.S. Cl.
USPC .......................................... 540/523

(58) Field of Classification Search
USPC .......................................... 540/523
See application file for complete search history.

(56) References Cited

U.S. PATENT DOCUMENTS 8,097,720 B2 * 1/2012 Peglion et al. ............... 540/523
8,415,468 B2 * 4/2013 Peglion et al. ............... 540/523

* cited by examiner

*Primary Examiner* — Bruck Kifle
(74) *Attorney, Agent, or Firm* — Hueschen and Sage

(57) ABSTRACT

Process for the synthesis of ivabradine of formula (I):

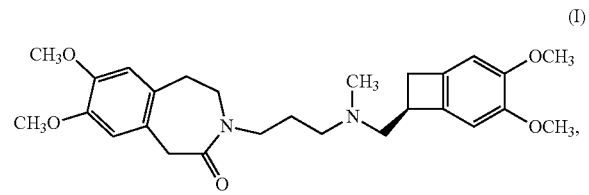

addition salts thereof with a pharmaceutically acceptable acid, and hydrates thereof.

5 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

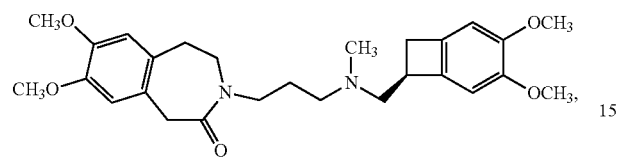

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
addition salts thereof with a pharmaceutically acceptable acid, and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859. Unfortunately, the ivabradine synthesis route described in that patent specification results in the expected product in a yield of only 1%.

Another ivabradine synthesis route, which is based on a reductive amination reaction, has been described in the European patent specification EP 1 589 005.

Reductive amination is a route that is a favoured approach for preparing amines. As this approach does not require isolation of the intermediate imine formed, this coupling reaction between an aldehyde and an amine in the presence of a reducing agent is widely used for the synthesis of compounds that are of value in the pharmaceutical or agrochemical fields and also in materials science.

The procedural protocols conventionally employed for carrying out reductive amination are:
either use of stoichiometric amounts of hydride donors such as borohydrides ($NaBH_4$, $NaBH_3CN$ or $NaBH(OAc)_3$),
or catalytic hydrogenation.

The use of hydride donors generates numerous waste products and the reagents in themselves are toxic.

In the case of catalytic hydrogenation, the fact that the reducing agent is molecular hydrogen is certainly of environmental value. The synthesis described in patent specification EP 1 589 005 follows this second route.

The patent specification EP 1 589 005 namely describes the synthesis of ivabradine hydrochloride starting from the compound of formula (II):

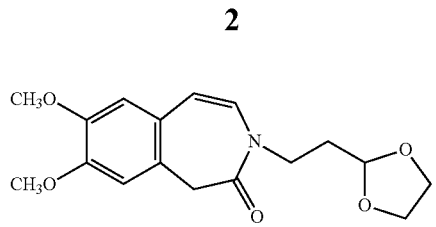

which is subjected to a catalytic hydrogenation reaction in the presence of hydrogen and a palladium catalyst to yield the compound of formula (III):

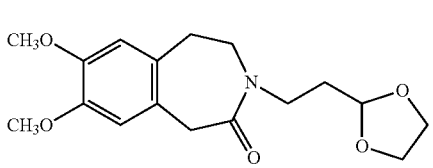

which, without being isolated, is reacted, in the presence of hydrogen and a palladium catalyst, with the compound of formula (IV):

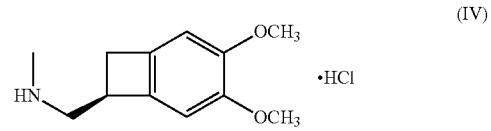

to yield ivabradine of formula (I), in hydrochloride form.

The disadvantage of that synthesis route is the use of a palladium catalyst.

Palladium, like rhodium, ruthenium or iridium, metals that are likewise used for catalysing reductive amination reactions, is a precious metal, the limited availability—and consequently high price—and also the toxicity of which limit its acceptability.

The present Application describes an ivabradine synthesis route which makes it possible to dispense with the use of a borohydride or a precious metal.

The present invention relates to a process for the synthesis of ivabradine of formula (I):

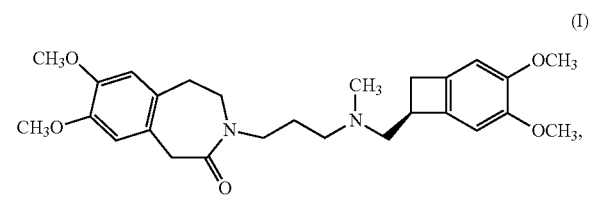

characterised in that the compound of formula (V):

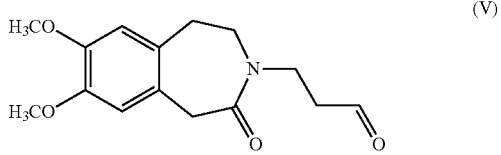 [SMILES: COc1cc2c(cc1OC)CC(=O)N(CCC=O)CC2]

is subjected to a reductive amination reaction with the compound of formula (VI):

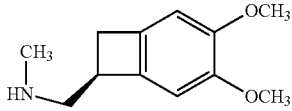

in the presence of triethylamine and formic acid,
in the absence of solvent or in an alcoholic solvent.

The use of formic acid as reducing agent (Leuckart-Wallach reaction) sometimes requires very elevated temperatures, possibly reaching 180° C., and the secondary formation of N-formyl type compounds is often observed.

The amount of formic acid used in the reaction for the reductive amination of the compound of formula (V) with the compound of formula (VI) is greater than 1 equivalent per equivalent of aldehyde, more preferably from 2 to 50 equivalents per equivalent of aldehyde.

The amount of triethylamine used in the reaction for the reductive amination of the compound of formula (V) with the compound of formula (VI) is greater than 1 equivalent per equivalent of aldehyde, more preferably from 2 to 50 equivalents per equivalent of aldehyde.

The temperature of the reductive amination reaction between the compound of formula (V) and the compound of formula (VI) is preferably from 15 to 100° C., more preferably from 30 to 100° C.

Among the alcoholic solvents that may possibly be used for carrying out the reaction for the reductive amination of the compound of formula (V) with the compound of formula (VI) there may be mentioned, without implying any limitation, ethanol, isopropanol or trifluoroethanol.

The Example hereinbelow illustrates the invention.

The column chromatography purification procedures are carried out on 70-230 mesh silica gel.

The $^1$H NMR spectra are recorded at 400 MHz.

The chemical shifts are expressed in ppm (internal reference: TMS).

The following abbreviations have been used to describe the peaks: singlet (s), doublet (d), doublet of doublets (dd), triplet (t), quadruplet (q), multiplet (m).

EXAMPLE 1

3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzazepin-2-one In a clean and dry Schlenk tube, 0.25 mmol of 3-(7,8-dimethoxy-2-oxo-1,2,4,5-tetrahydro-3H-3-benzazepin-3-yl) propanal, 0.25 mmol of [(7S)-3,4-dimethoxybicyclo[4.2.0] octa-1,3,5-trien-7]-N-methylmethanamine and 1 mL (7.4 mmol) of triethylamine are stirred at ambient temperature under an argon atmosphere for one hour.

113 μL (3 mmol) of formic acid are added cautiously and the mixture is heated at 85° C. for 18 hours. After cooling to ambient temperature, the reaction mixture is diluted with 5 mL of 3M aqueous sodium hydroxide solution. The aqueous phase is extracted three times with 5 mL of ethyl acetate. The organic phases are combined, washed with saturated aqueous NaCl solution (10 mL), dried over MgSO$_4$ and evaporated under reduced pressure.

The crude product is purified on silica gel (eluant: pentane/ethyl acetate (95/5)) to obtain the expected product.

Yield=62%

$^1$H NMR (CDCl$_3$): δ=6.67 and 6.64 (2s, 2H); 6.55 and 6.50 (2s, 2H); 3.79 and 3.78 (2s, 12H); 3.76 (s, 2H); 3.67 (m, 2H); 3.45 (m, 3H); 3.17 (dd, 1H); 2.99 (m, 2H); 2.65 (m, 2H); 2.50 (dd, 1H); 2.37 (t, 2H); 2.26 (s, 3H); 1.72 (q, 2H).

The invention claimed is:

1. A process for the synthesis of ivabradine of formula (I):

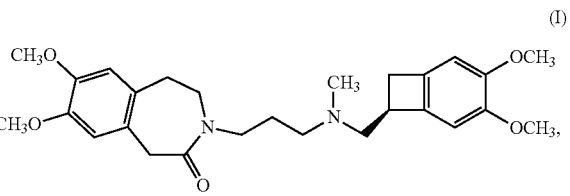

wherein a compound of formula (V):

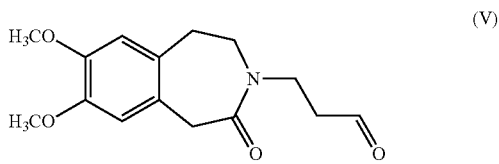

is subjected to a reductive amination reaction with an amine of formula (VI):

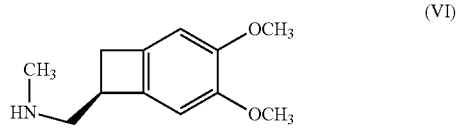

in the presence of formic acid in an amount greater than 1 equivalent per equivalent of aldehyde
and of triethylamine in an amount greater than 1 equivalent per equivalent of aldehyde,
at a temperature from 15 to 100° C.,
in the absence of solvent or in an alcoholic solvent.

2. The process according to claim 1, wherein the reductive amination reaction is carried out in the absence of solvent.

3. The process according to claim 1, wherein the amount of formic acid used in the reductive amination reaction is from 2 to 50 equivalents per equivalent of aldehyde.

4. The process according to claim 1, wherein the amount of triethylamine used in the reductive amination reaction is from 2 to 50 equivalents per equivalent of aldehyde.

5. The process according to claim 1, wherein the temperature of the reductive amination reaction is from 30 to 100° C.

* * * * *